(12) United States Patent
Douglas et al.

(10) Patent No.: US 6,939,884 B2
(45) Date of Patent: Sep. 6, 2005

(54) PHARMACEUTICAL AGENTS CONTAINING ACYCLOVIR, FUSARIC ACID AND DERIVATIVES THEREOF

(75) Inventors: Michael G. Douglas, St. Louis, MO (US); Avinash N. Amin, St. Louis, MO (US)

(73) Assignee: Novactyl, Inc., St. Louis, MO (US)

( * ) Notice: Subject to any disclaimer, the term of this patent is extended or adjusted under 35 U.S.C. 154(b) by 0 days.

(21) Appl. No.: 10/310,614

(22) Filed: Dec. 3, 2002

(65) Prior Publication Data

US 2003/0139370 A1 Jul. 24, 2003

Related U.S. Application Data

(63) Continuation of application No. 09/903,337, filed on Jul. 11, 2001, now Pat. No. 6,569,864.

(51) Int. Cl.[7] .................. A01N 43/40; A01N 43/90; A01N 31/50
(52) U.S. Cl. ................ 514/354; 514/262.1; 514/252.11
(58) Field of Search ............................ 514/354, 262.1, 514/252.11, 262

(56) References Cited

U.S. PATENT DOCUMENTS 5,767,135 A * 6/1998 Fernandez-Pol
6,127,393 A * 10/2000 Fernandez-Pol

OTHER PUBLICATIONS

Physicians Desk Reference, Ed. 51, 1997, pp. 1187–1194.*
Transfusion Science, vol. 23, n 3, Dec. 2000 (249–250); "Combining iron chelators with the nucleoside analog didanosine in anti–HIV Therapy"; by Georgiou, Niki A. et al.

Journal of Chemotherapy, vol. 5, –n. 1 (3–9) 1993: Mode of Action of Zn–Complexes on Herpes Simplex Virus Type 1 Infection in Vitro; by T.L. Varadinova, P.R. Bonchev; C.K. Nachev; S.A. Shishkov; D. Strachilov; Z. Paskalev; A. Toutekova and M. Panteva.

Journal of Pharmaceutical Sciences, vol. 77 n 4, Apr. 1988 (285–298) : Glycolamide Esters as Biolabile Prodrugs of Carboxylic Acid Agents: Synthesis, Stability, Bioconversion, and Physicochemical Properties; by Neils Mork Nielsen and Hans Bungaard.

Handbook of Animal Models of Infection 1988, Aug.; 9 (5) 911–918; Animal Models of Herpes Skin Infection: Guinea–pig by Spruance SL, McKeough MB.

Journal of Pharmaceutical Sciences, an.1977; vol. 66 (1): 1–19. Pharmaceutical Salts; Berge SM, Bighley LD et al.

Anticancer Research 21:931–958 (2001) Essential Viral and Cellular Zinc and Iron Containing Metalloproteins as Targets for Novel Antiviral and Anticancer Agents: Implications for Prevention and Therapy of Viral Diseases and Cancer; J. Alberto Fernandez–Pol, Paul D. Hamlton and Dennis J. Klos.

* cited by examiner

Primary Examiner—San-Ming Hui
(74) Attorney, Agent, or Firm—Thompson Coburn LLP (57) ABSTRACT

Compositions are provided, which comprise at least one nucleoside analogue inhibitor, pharmaceutically acceptable salts, solvates, or prodrugs thereof and fusaric acid, derivatives, or pharmaceutically acceptable salts thereof. Pharmaceutical compositions comprising the above compositions are also provided that optionally further include another therapeutically effective compound, such as a carrier. Systemic and topical preparations comprising the above compositions are also provided as well as methods of treating viral diseases by the administration of the above antiviral agents to a patient.

4 Claims, 2 Drawing Sheets

The antiviral effect of fusaric acid on HSV as determined by plaque reduction assay.

Fig. 1 The antiviral effect of fusaric acid on HSV as determined by plaque reduction assay.

Fig. 2. The cytotoxicity profile of fusaric acid as determined by neutral red uptake assay.

PHARMACEUTICAL AGENTS CONTAINING ACYCLOVIR, FUSARIC ACID AND DERIVATIVES THEREOF

CROSS-REFERENCES TO RELATED APPLICATIONS

This is a continuation of U.S. patent application Ser. No. 09/903,337, filed Jul. 11, 2001 now U.S. Pat. No. 6,569,864.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

This invention relates to pharmaceutical agents for the treatment of viral diseases, and more specifically, to pharmaceutical agents containing acyclovir and fusaric acid or derivatives thereof.

BACKGROUND OF THE INVENTION

Acyclovir, 2-amino-1,9-dihydro-9-[(2-hydroxyethoxy) metyl]-6H-purin-6-one, has been used for the inhibition of herpes simplex virus types 1 (HSV-1), 2 (HSV-2), and varicella-zoster virus (VZV). Acyclovir is a synthetic purine nucleoside analogue with in vitro and in vivo inhibitory activity against HSV-1, HSV-2 and VZV, which can be found in capsule, tablet, topical and suspension formulations. The following structural formula represents acyclovir:

The inhibitory activity of acyclovir is highly selective due to its affinity for the enzyme thymidine kinase encoded by HSV-1, HSV-2 and VZV. This viral enzyme converts acyclovir into acyclovir monophosphate, a nucleotide analogue. The monophosphate is further converted into diphosphate by cellular guanylate kinase and into triphosphate by a number of cellular enzymes. In vitro, acyclovir triphosphate stops replication of herpes viral DNA. This is accomplished by: 1) competitive inhibition of viral DNA polymerase, 2) incorporation into and termination of the growing viral DNA chain and 3) inactivation of the viral DNA polymerase.

While the use of acyclovir is useful in the treatment of some herpes viruses, it has limitations related to tissue permeability and viral resistance that make its use less desirable. For example, acyclovir is not effective in topical formulation against herpes labialis and herpes genitalis. As such, acyclovir may not be used topically to effectively treat herpes labialis, herpes genitalis or other viral diseases, disorders, or conditions. Moreover, prodrugs of acyclovir have only minimal effects in herpes labialis. For example, the use of denavir to treat herpes labialis reduces the median duration of the illness by 6 hours. However, herpes labialis typically lasts in the range of about 6 to 7 days. Also, viral strains resistant to acyclovir and its prodrugs have emerged, which further limit its clinical usefulness.

Accordingly, there is a need to provide compositions that may be used topically to successfully treat a wide range of viral diseases.

SUMMARY OF THE INVENTION

In overcoming the above disadvantage, it is an object of the invention to produce compositions, which may be used topically to successfully treat a wide range of viral diseases.

Accordingly, and in one aspect of the invention, a composition including at least one nucleoside analogue inhibitor, a pharmaceutically acceptable salt, solvate, or prodrug thereof and fusaric acid, a derivative, or pharmaceutically acceptable salt of fusaric acid is provided.

In a second aspect, a pharmaceutical composition comprising the above-described composition of the invention and a pharmaceutically acceptable carrier is provided.

In a third aspect, a method of treating a viral disease, disorder, or condition comprising the administration of a pharmaceutically effective dose of the above-described pharmaceutical composition to a patient is provided.

In a fourth aspect, a topical preparation is provided that includes at least one above-described composition of the invention and a liquid vehicle.

In a fifth aspect, a systemic preparation is provided that includes at least one above-described pharmaceutical composition.

Other objects and features will be in part apparent and in part pointed out hereinafter.

DETAILED DESCRIPTION OF THE INVENTION

In accordance with the present invention, it has been discovered that a composition can be prepared, which can be used to successfully treat a wide range of viral diseases. The composition of the invention comprises fusaric acid, or any pharmacologically acceptable salt or derivative thereof and at least one nucleoside analogue inhibitor or a pharmaceutically acceptable salt, solvate or prodrug thereof. Fusaric acid is the 5-butyl derivative of picolinic acid. As used herein, "nucleoside analogue inhibitor" includes any pharmaceutically acceptable salt, solvate, or prodrug of a nucleoside analogue inhibitor. The structure of fusaric acid and many of its derivatives is represented by the following structure (formula (I)):

wherein $R_1$, $R_2$ and $R_4$ are selected from the group consisting of a peptide of sixteen amino acids, carboxyl group, methyl group, ethyl group, propyl group, isopropyl group, butyl group, isobutyl group, secondary butyl group, tertiary butyl group, pentyl group, isopentyl group, neopentyl group, fluorine, chlorine, bromine, iodine, and hydrogen and $R_3$ is a butyl group. As used herein, "fusaric acid" includes the above-derivatives thereof.

As used herein, "pharmaceutically acceptable" means it is, within the scope of sound medical judgment, suitable for use in contact with the cells of humans and lower animals without undue toxicity, irritation, allergic response and the like, and is commensurate with a reasonable benefit/risk ratio. As used herein, "animal" includes humans. "Pharmaceutically acceptable salt" means a relatively non-toxic, inorganic and organic acid addition salt, or base addition salt of compounds of the invention. These salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include, but are not limited to the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulphamates, malonates, salicylates, propionates, methylene-bis-b-hydroxynaphthoates, gentisates, isethionates, di-p-toluoyltartrates, methane-sulphonates, ethanesulphonates, benzenesulphonates, p-toluenesulphonates, cyclohexylsulphamates and quinateslaurylsulphonate salts and the like. Other suitable salts are found in S. M. Berge, et al., "Pharmaceutical Salts," J. Pharm. Sci., 66: p.1–19 (January 1977), which is incorporated herein by reference in its entirety.

Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium and aluminum salts. Suitable inorganic base addition salts are prepared from metal bases which include, but are not limited to sodium hydride, sodium hydroxide, potassium hydroxide, calcium hydroxide, aluminum hydroxide, lithium hydroxide, magnesium hydroxide and zinc hydroxide. Suitable amine base addition salts are prepared from amines which have sufficient basicity to form a stable salt, and preferably include those amines which are frequently used in medicinal chemistry because of their low toxicity and acceptability for medical use. Suitable amine base addition salts include, but are not limited to, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine dicyclohexylamine and the like.

Fusaric acid was recognized in the early 1960's to have activity as an antihypertensive agent in vivo. It also has been shown that fusaric acid is an inhibitor of cancerous cell growth, showing an effect on the growth and viability of normal and cancerous cells in tissue culture. U.S. Pat. Nos. 5,767,135 and 6,127,393, herein incorporated by reference in their entireties, show the usefulness of fusaric acid as a potent anti-cancer and anti-viral agent in vivo.

Figure 1:
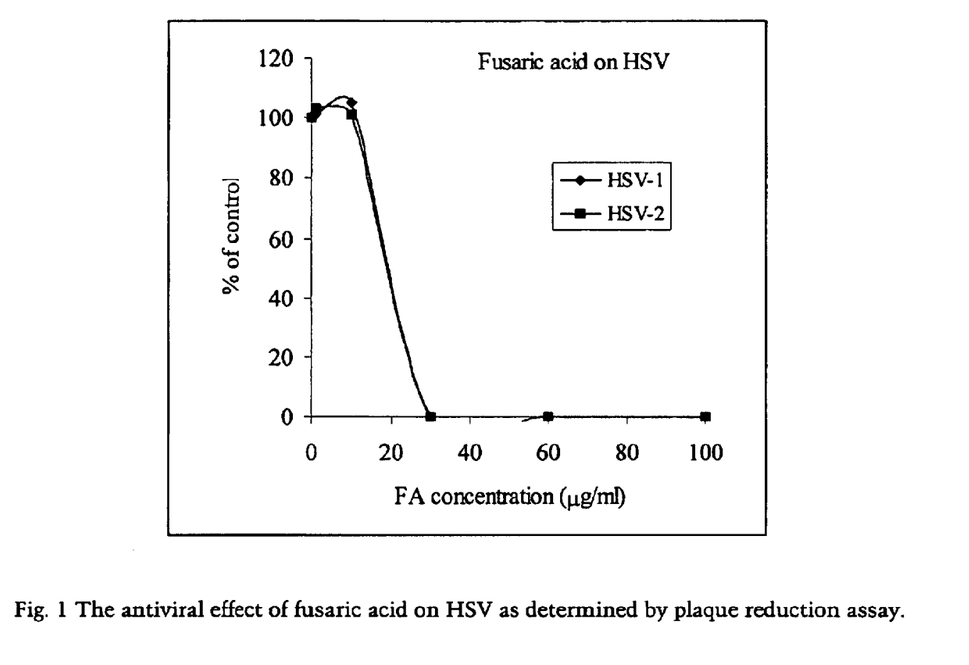
FIG. 1 illustrates the antiviral effect of fusaric acid on HSV as determined by plaque reduction assay.
Figure 2:
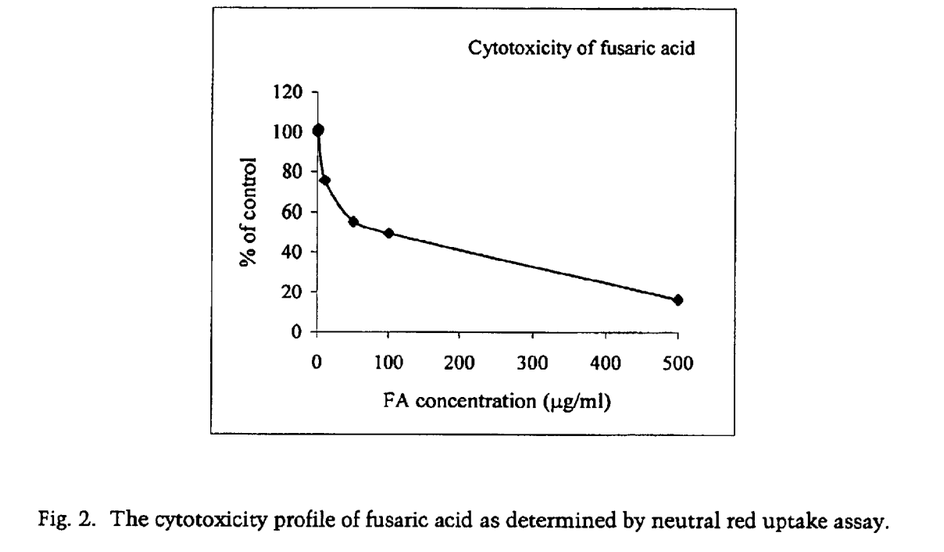
FIG. 2 illustrates the cytotoxicity profiles of fusaric acid as determined by neutral red uptake assay.

It has now been discovered that when fusaric acid, a derivative, or pharmaceutically acceptable salt thereof is combined with at least one nucleoside analogue inhibitor, pharmaceutically acceptable salt, solvate or prodrug thereof, a synergistic antiviral effect is observed. For example, FIGS. 1 and 2 illustrate the antiviral effect of fusaric acid on HSV-1 and HSV-2 as determined by plaque reduction assay, a technique described in detail below. The 50% effective concentration of fusaric acid was approximately 19 $\mu$g/ml for HSV-1 and 18 $\mu$g/ml for HSV-2. The effective concentration giving 90-100% plaque reduction was approximately 30 $\mu$g/ml for both HSV-1 and HSV-2.

Fusaric acid is active against HSV-1 and HSV-2 infections. However, as demonstrated in Example 3 below, the addition of small amounts of acyclovir or another nucleoside analogue inhibitor to fusaric acid, a derivative, or pharmaceutically acceptable salt thereof results in enhanced antiviral effects as compared to the antiviral effects of either fusaric acid or acyclovir alone. Specifically, and with reference to Example 3 below, administration of the compositions of the invention comprising both fusaric acid and acyclovir to susceptible cells show about a 50% reduction of HSV-1 viral activity and about a 40% reduction in HSV-2 viral activity.

The compositions of the invention are prepared by admixing each component. In embodiments employing additional compounds, elevated temperature may be necessary to ensure uniform dispersement of the pharmacologically active components through the chosen medium. Generally, uniform disbursement of the components occurs at a temperature of about 45° C. However, one skilled in the art can readily determine, without undue experimentation, the exact conditions necessary to prepare the compositions of the invention, which may vary depending on the specific composition employed, the nature and presence of other therapeutic compositions or carriers within the composition of the invention and the quantity being produced. The compounds of the invention may alternatively be prepared by other methods well known in the art.

At least one nucleoside analogue inhibitor, pharmaceutically acceptable salt, solvate, or prodrug thereof must be present in the compositions of the invention. Suitable nucleoside analogue inhibitors include, but are not limited to acyclovir, zidovudine, didanosine, zalcitabine, lamivudine, stavudine, abacavir, combivir, valacyclovir, famciclovir, ganciclovir, ribavirin and denavir. In one embodiment, the compositions of the invention comprise acyclovir, or a pharmaceutically acceptable salt, solvate, or prodrug thereof. In a specific embodiment of the invention, the nucleoside analogue inhibitor is an acyclic guanosine analogue. Suitable acyclic guanosine analogues include, but are not limited to acyclovir, valacyclovir, famciclovir, gangciclovir and denavir. As used herein, denavir may be optionally referred to as penciclovir.

Pharmaceutically acceptable prodrugs are those prodrugs of the compounds that are within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compositions of the invention. The term "prodrug" means compounds that are rapidly transformed in vivo to yield the parent compound of the above formula, for example by hydrolysis in blood. Functional groups which may be rapidly transformed, by metabolic cleavage, in vivo form a class of groups reactive with the carboxyl group of the compositions of this invention. They include, but are not limited to such groups as alkanoyl (such as acetyl, propionyl, butyryl, and the like), unsubstituted and substituted aroyl (such as benzoyl and substituted benzoyl) alkoxycarbonyl (such as ethoxycarbonyl), trialkylsilyl (such as trimethyl- and triethysilyl) monoesters formed with dicarboxylic acids (such as succinyl) and the like. Because of the ease with which the metabolically cleavable groups of the compounds useful according to this invention are cleaved in vivo, the compounds bearing such groups act as pro-drugs. The compounds bearing the metabolically cleavable groups have the advantage that they may exhibit improved bioavailability as a result of enhanced solubility and/or rate of absorption conferred upon the parent compound by virtue of the presence of metabolically cleavable group. A thorough discussion of prodrugs is provided in Glycolamide esters as biolabile prodrugs of carboxylic acid agents: synthesis, stability, bioconversion, and physicochemical properties, Nielsen N M, Bundgaard H., J Pharm Sci. 1988 April;77(4) :285-98, which is incorporated herein by reference.

The relative concentrations of fusaric acid and acyclovir in the compositions of the invention are dependent upon the specific usage for the compositions of the invention, e.g. the nature of the disease and the relative age, condition and size of the patient, as well as the method of administration and/or carrier employed. Generally, the compositions of the invention comprise about 0.2% to about 50% fusaric acid, a pharmaceutically acceptable salt, or derivative thereof and in the range of about 0.2% to 50% at least one nucleoside analogue inhibitor. In another embodiment, the compositions of the invention comprise about 1% to about 20% fusaric acid, a pharmaceutically acceptable salt, or derivative thereof and in the range of about 1% to about 20% at least one nucleoside analogue inhibitor. In yet another embodiment, the compositions of the invention comprise about 5% fusaric acid, a pharmaceutically acceptable salt, or derivative thereof and about 5% at least one nucleoside analogue inhibitor. It will be appreciated by those of skill in the art that compositions including a combination of nucleoside analogue inhibitors are within the scope of the present invention. It will also be appreciated by those of skill in the art that compositions having concentrations outside of the stated ranges are within the scope of the present invention.

In one specific embodiment, the composition of the invention comprises about 5% acyclovir and about 5% fusaric acid. This particular formulation of the invention has been shown to effectively treat primary HSV-1 infection in vivo. See Example 4, supra.

The foregoing compositions of the invention may also be mixed with other compounds to form pharmaceutical compositions (with or without diluent or carrier) which, when administered, provide simultaneous administration of a combination of active ingredients resulting in the combination therapy of the invention. Accordingly, and in one aspect of the invention, a pharmaceutical composition is provided comprising the above-described compositions of the invention and at least one other compound selected from the group consisting of pharmaceutically acceptable carriers, diluents, for example saline solutions, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents, dispensing agents and any combination thereof. The compound may also be a liquid vehicle, including but not limited to both an ointment and absorption base. The compound employed depends on the nature of the disease, mode of administration, dosage forms employed, as well as the overall age, size and condition of the patient. Examples of suspending agents include, but are not limited to, ethoxylated isostearyl alcohols, polyoxyethylene sorbitol and sorbitan esters, microcrystalline cellulose, aluminum metahydroxide, bentonite, agar-agar and tragacanth and any combination or mixture of these substances.

In certain preferred embodiments, active ingredients necessary in combination therapy may be combined in a single pharmaceutical composition for simultaneous administration.

The choice of vehicle and the content of active substance in the vehicle are also generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulfate and talc may be used for preparing tablets. When aqueous suspensions are used they can contain emulsifying agents or agents that facilitate suspension. Diluents such as sucrose, ethanol, polyethylene glycol, propylene glycol, glycerol and chloroform or mixtures thereof may also be used.

Any pharmaceutically acceptable carrier suitable to permit drug administration may be used. Suitable carriers include, but are not limited to colorants, flavorants, and other inactive or inert ingredients, for example, gelatin, corn starch, lactose, magnesium stearate, sodium lauryl sulfate, parabens, ink, microcrystalline cellulose, povidone, methyl paraben, preservatives and sodium starch glycolate.

The pharmaceutical compositions of the invention are administered to a patient by any acceptable mean that results in effective antiviral activity according to the methods of the invention. Acceptable means of administration include, but are not limited to topical, oral, parenteral, subcutaneous, intravenous, vaginal, intramuscular, systemic and intraperitoneal administration. Accordingly, the pharmaceutical compositions of the invention may be administered to a patient, among other routes of administration, in capsule forms, topical preparations or intravaginal preparations. As used herein, "patient" includes both humans and other animals. It will be appreciated that the preferred route may vary with, for example, the nature of the disease and the condition, age and size of the patient.

Topical preparations are provided in accordance with the invention, which comprise the above-described compositions of the invention and a liquid vehicle. Formulations suitable for topical administration are formulations that are in a form suitable to be administered topically to a patient. The formulation may be presented as a topical ointment, salves, powders, sprays and inhalants, gels (water or alcohol based), creams, as is generally known in the art, or incorporated into a matrix base for application in a patch, which would allow a controlled release of compound through the transdermal barrier. When formulated in an ointment, the active ingredients may be employed with either a paraffinic or a water-miscible ointment base. Alternatively, the active ingredients may be formulated in a cream with an oil-in-water cream base. Formulations suitable for topical administration in the eye include eye drops wherein the active ingredient is dissolved or suspended in a suitable carrier, especially an aqueous solvent for the active ingredient. Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier. The liquid carrier may be any liquid carrier suitable to facilitate the topical application of the compositions of the invention. Suitable liquid vehicles include but are not limited to ointment and absorption bases.

The relative concentrations of fusaric acid and nucleoside analogue inhibitor in the topical preparations of the invention are dependent upon the specific usage for the composition of the invention, e.g. the nature of the disease and the relative age, condition and size of the patient, as well as the method of administration and/or carrier employed. Generally, the topical preparations of the invention comprise about 0.2% to about 50% fusaric acid and in the range of about 0.2% to 50% at least one nucleoside analogue inhibitor. In another embodiment, the topical and intravaginal preparations of the invention comprise about 1% to about 20% fusaric acid, a pharmaceutically acceptable salt, or derivative thereof and about 1% to about 20% at least one nucleoside analogue inhibitor. In yet another embodiment, the topical and intravaginal preparations of the invention comprise about 5% fusaric acid, a pharmaceutically acceptable salt, or derivative thereof and about 5% at least one nucleoside analogue inhibitor. It will be appreciated by those of skill in the art that compositions including a combination of nucleoside analogue inhibitors are within the scope of the present invention. It will also be appreciated by those of skill in the art that compositions having concentrations outside of the stated ranges are within the scope of the present invention.

In one specific embodiment, the topical preparations of the invention comprise about 5% acyclovir and about 5% fusaric acid. This particular formulation of the invention has been shown to effectively treat HSV-1 in vivo. See Example 4, supra.

If desired, and for more effective distribution, the compounds of the invention can be microencapsulated in, or attached to, a slow release or targeted delivery systems such as a biocompatible, biodegradable polymer matrices, e.g. poly(d,1-lactide co-glycolide), liposomes, and microspheres and subcutaneously or intramuscularly injected by a technique called subcutaneous or intramuscular depot to provide continuous slow release of the compounds for a period of 2 weeks or longer. The compounds may be sterilized, for example, by filtration through a bacteria retaining filter, or by incorporating sterilizing agents in the form of sterile solid compositions which can be dissolved in sterile water, or some other sterile injectable medium immediately before use.

Formulations suitable for systemic administration are formulations that are in a form suitable to be administered systemically to a patient. The systemic formulation of the invention includes the above-described compositions of the invention and at least one other compound, preferably a liquid vehicle. The formulation is preferably administered to a patient by injection, including transmuscular, intravenous, intraperitoneal, and subcutaneous. For injection, the compounds useful according to the invention are formulated in liquid solutions, e.g., saline solutions, and preferably, in physiologically compatible buffers such as Hank's solution or Ringer's solution. In addition, the compounds may be formulated in solid form and redissolved or suspended immediately prior to use. Lyophilized forms are also included.

Systematic administration also can be by transmucosal or transdermal means, or the compounds can be administered orally. For transmucosal or transdermal administration, penetrants appropriate to the barrier to be permeated are used in the formulation. Such penetrants are generally known in the art, and include, for example, bile salts and fusaric acid derivatives for transmucosal administration. In addition, detergents may be used to facilitate permeation. Transmucosal administration may be through use of nasal sprays, for example, or suppositories. For oral administration, the compounds are formulated into conventional oral administration forms such as capsules, tablets, and tonics.

A therapeutically effective dose of the compositions of the invention are administered to patients according to the methods of the invention. A therapeutically effective dose is the dosage necessary to provide the desired physiological change, i.e., to kill the subject virus. The compositions of the invention can be prepared in unit dosage form by any of the methods well known in the art of pharmacy. The specific dosage, however, is dependent upon the means of administration, the general health and physical condition of the patient, as well as the patient's age and weight, and the specific viral disease, disorder, or condition suffered by the patient. The existence of other concurrent treatments may also effect the specific dosage administered to the patient.

The amount of composition of the invention administered to a patient is also determined by the attending clinicians taking into consideration the etiology and severity of the disease, the patient's condition, size and age, the potency of each component and other factors.

The compositions of the invention may be presented in unit-dose or multi-dose containers, for example sealed ampoules and vials with elastomeric stoppers, and may be stored in freeze-dried condition requiring only the addition of the sterile liquid carrier, for example water for injections, immediately prior to use. Extemporaneous injection solutions and suspensions may be prepared from sterile powders, granules and tablets of the kind previously described.

The compositions of the invention are prepared as described herein or by the application or adaptation of known methods, by which is meant methods used heretofore or described in the literature.

The invention also provides kits or single packages combining two or more active ingredients useful in treating the disease. A kit may provide alone, or in combination with a pharmaceutically acceptable diluent or carrier, the above-described formula (I) and the above-described nucleoside analogue inhibitor, pharmaceutically acceptable salt, solvate or prodrug thereof, alone, or in combination with a diluent or carrier.

The compositions of the invention optionally are supplied as salts. Those salts which are pharmaceutically acceptable are of particular interest since they are useful in administering the foregoing compounds for medical purposes. Salts that are not pharmaceutically acceptable are useful in manufacturing processes, for isolation and purification purposes, and in some instances, for use in separating stereoisomeric forms of the compounds of this invention. The latter is particularly true of amine salts prepared from optically active amines.

All references and patents cited herein are hereby incorporated by reference in their entireties for their relevant teachings. Accordingly, any reference cited herein and not specifically incorporated by reference is, nevertheless, incorporated by reference in its entirety as if part of the specification.

The following examples are illustrative of specific embodiments of the invention and do not limit the scope of the invention in any way. In each example, the plaque reduction technique and cytotoxicity testing procedures described with reference to Example 1 are used to determine the percent of control of the samples (% of control).

EXAMPLE 1

Antiviral Effect of Fusaric Acid on HSV-1 and HSV-2

A stock solution (200 mg/ml) of fusaric acid was dissolved in dimethyl sulfoxide (DMSO), aliquoted, and stored in a freezer (−20° C.).

Herpes simplex virus (HSV) standard strains G (HSV-2) and F (HSV-1) were used in the experiments. Virus input for a 6-well plate was 100 pfu/well. HSV susceptible cell lines, Vero cells, were used in the virus yield reduction assay. The culture medium for Vero cells is 5% MEM (Minimum Essential Medium GIBCO/BRL) supplemented with 5% fetal bovine serum, 100 U/ml penicillin and 100 μg/ml streptomycin.

The antiviral effects of picolinic acid and fusaric acid were determined by plaque reduction assay. Confluent cells were washed with PBS and subsequently infected with either HSV-1 or HSV-2 (100 pfu/well) for 1 hour (h) at 37° C. and tilting every 10 min. After viral inoculum was removed, infected cells were washed with PBS and overlaid with 0.5% methylcellulose in culture medium (equal volume of 1% methylcellulose mixed with 2×culture medium) containing different doses of testing compounds. The cells were incubated at 37° C. for 2 days for HSV-2 infected cells and 3 days for HSV-1 infected cells. When plaque size was adequate, the cells were fixed with 10% formalin for 10 min. The plaques were subsequently stained with 0.5% crystal violet for 10 min. The dye was removed by washing with tap water and left to dry in a fume hood. The plaques were then counted by hand, which resulted in an error of margin of about ±5.

All data were generated from duplicate or triplicate experiments. Mean plaque counts in test wells were compared with mean plaque counts in control wells (without compound). Effects of compounds at varying concentrations were expressed as % of control (the mean plaque counts in drug-treated wells/the mean plaque counts in control wells). $EC_{50}$'s (concentrations giving a 50% reduction in the plaque count of the inoculum) were calculated using Statview™.

The testing concentrations for fusaric acid were 0, 1, 10, 30, 60, 100 μg/ml based on initial observation that 200–500 μg/ml of fusaric acid was toxic to cells.

The results are shown in Table 1 below.

TABLE 1

| | | Fusaric acid | | | | | |
|---|---|---|---|---|---|---|---|
| | Conc. (μg/ml) | 0 | 1 | 10 | 30 | 60 | 100 |
| HSV-1 | Mean plaques | 67.5 | 68.5 | 71 | 0 | 0 | 0 |
| | % of control | 100 | 101 | 105 | 0 | 0 (+) | 0 (++) |
| HSV-2 | Mean plaques | 94 | 97 | 95 | 0 | 0 | 0 |
| | % of control | 100 | 103 | 101 | 0 | 0 (+) | 0 (++) |

+: ~20% cell death observed under microscope.
++: ~50% cell death observed under microscope.

The $EC_{50}$ of fusaric acid was approximately 19 μg/ml for HSV-1 and 18 μg/ml for HSV-2. The $EC_{90-100}$ was approximately 30 μg/ml for both HSV-1 and -2.

EXAMPLE 2

Cytotoxicity Profiles of Picolinic Acid and Fusaric Acid

The cytotoxic effects of picolinic acid and fusaric acid were examined on Vero cells using neutral red dye uptake assay. Confluent Vero cells were cultured in a medium containing various doses of picolinic acid for two days. The testing concentrations were 0, 10, 100, 250, 500 and 1000 μg/ml for picolinic acid and 0, 1, 10, 50, 100 and 500 μg/ml for fusaric acid. Culture medium was removed from confluent Vero cells in a 96-well plate by pump. The cells were then washed once with 200 μl of PBS. 200 μl culture medium containing varying concentrations of either picolinic acid or fusaric acid was added to each well. The cells were then incubated with 0.01% neutral red dye at 37° C. for two days. At the end of incubation, the medium was removed and the cells washed with PBS. 200 μl of 0.01% neutral red in PBS was subsequently added to each well and incubated at 37° C. for 30 minutes The dye was then removed and the cells washed twice with 200 μl PBS per well. The dye was extracted by addition of 200 μl of 50% ethanol/1% glacial acetic acid in PBS to each well and incubated at room temperature for 15 minutes with gentle shaking at 120–150 rpm. The absorbance at 550 nm was read on an enzyme-linked immunosorbent assay (ELISA) reader. The toxicity profiles of picolinic acid and fusaric acid on Vero cells analyzed from optical absorbance readings are shown in Table 2.

TABLE 2

| Cytotoxicity of Picolinic Acid and Fusaric Acid | | | | | | |
|---|---|---|---|---|---|---|
| Picolinic acid (μg/ml) | 0 | 10 | 100 | 250 | 500 | 1000 |
| Toxicity (% of control) | 100 | 105 | 95 | 70 | 57 | 45 |
| Fusaric acid (μg/ml) | 0 | 1 | 10 | 50 | 100 | 500 |
| Toxicity (% of control) | 100 | 101 | 76 | 55 | 49 | 16 |

The cytotoxic concentration giving 50% of cell death ($CC_{50}$) was approximately 800 μg/ml for picolinic acid and 100 μg/ml for fusaric acid.

EXAMPLE 3

Drug Combination of Fusaric Acid and Acyclovir

To examine the efficacy of the combination of fusaric acid and acyclovir on HSV-1 and HSV-2 infected cells, the plaque reduction assay technique described in Example 1 was employed, except that either 1.75 μM or 6.1 μM of acyclovir was added to each sample of fusaric acid to test the combination against HSV-1 and HSV-2, respectively (with the exception of the control, which contained neither acyclovir, nor fusaric acid). Samples containing acyclovir only were also tested against HSV-1 and HSV-2.

The results are shown in Tables 3a and 3b below.

TABLE 3a

| | HSV-1 | | | | | |
|---|---|---|---|---|---|---|
| Fusaric acid (μg/ml) | 0 (Control) | 0 | 1 | 10 | 30 | 60 |
| Acyclovir (μM) | 0 (Control) | 1.75 | 1.75 | 1.75 | 1.75 | 1.75 |
| Mean plaques | 235 | 166 | 127 | 34 | 1 | 0 |
| | 277 | 156 | 106 | 31 | 1 | 1 |
| Average plaques | 256 | 161 | 116.5 | 32.5 | 1 | 0.5 |
| % of control | 100 | 62.9 | 45.5 | 12.7 | 0.4 | 0.2 |

TABLE 3b

| | | | HSV-2 | | | |
|---|---|---|---|---|---|---|
| Fusaric acid (μg/ml) | Control | 0 | 1 | 10 | 30 | 60 |
| Acyclovir (μM) | 0 | 6.1 | 6.1 | 6.1 | 6.1 | 6.1 |
| Mean plaques | 109 | 47 | 32 | 0 | 0 | 0 |
| | 110 | 47 | 33 | 3 | 0 | 0 |
| Average plaques | 109.5 | 47 | 32.5 | 1.5 | 0 | 0 |
| % of control | 100 | 42.9 | 29.7 | 1.4 | 0.0 | 0.0 |

With regard to HSV-1, the results indicate that 1.75 μM of acyclovir alone reduced the % of control by 37.1%, and decrease the plaque count from 256 (control) to 161. The results indicate that 1 μg/ml fusaric acid alone no effect on HSV-1 infected cells or plaque count. Although, the plaque count increased from 67.5 (control) to 68.5, the 1% increase in the % of control is within the error margin and can be attributed to human error.

However, the results indicate that the combination of 1.75 μM of acyclovir and 1 μg/ml fusaric acid reduced the % of control by 54.5%. The plaque count decreased from 256 (control) to 116.5. Since 1 μg/ml fusaric acid alone had no effect on HSV-1 infected cells, and 1.75 μM of acyclovir reduced the % of control by only 37.1% it is surprising that the % of control of the two agents in combination would be reduced by 54.5%. Because fusaric acid alone has no effect on HSV-1 infected cells, what would be expected is no improvement over acyclovir itself, or even a counter-additive effect. This 17.4% difference is beyond the error margin and clearly demonstrates synergy in the combination.

With regard to HSV-1, the results indicate that 1.75 μM of acyclovir alone reduced the % of control by 37.1%, and decreased the plaque count from 256 (control) to 161. The results indicate that 10 μg/ml of fusaric acid alone has essentially no effect on HSV-1 infected cells or plaque count. Although the % of control appeared to increase from 100 to 105, and the plaque count increased from 67.5 (control) to 71, these percentages are within the margin of error and can be attributed to human error.

However, the results indicate that the combination of 1.75 μM of acyclovir and 10 μg/ml fusaric acid reduced the % of control by 87.3%, and decreased the plaque count from 256 (control) to 32.5. Since 10 μg/ml fusaric acid alone had essentially no effect on HSV-1 infected cells, and 1.75 μM of acyclovir reduced the % of control by only 37.1%, it is surprising that the % of control of the two agents in combination would be reduced by 87.3%. Because 10 μg/ml fusaric acid alone has no effect on HSV-1 infected cells, what would be expected is no improvement over acyclovir by itself, or even a counter-additive effect. This 50.2% difference is beyond the error margin and clearly demonstrates synergy in the combination.

With regard to HSV-1, the results indicate that at concentrations ranging from 30 μg/ml to 100 μg/ml fusaric acid alone completely eliminated HSV-1 infected cells. The plaque counts were reduced from 67.5 (control) to 0 over the entire range. Since fusaric acid alone effectively resulted in complete cell death, the combination of fusaric acid in this range and acyclovir cannot show improvement at such high concentrations. The plaque counts simply cannot be reduced any further.

With regard to HSV-2, the results indicate that 6.1 μM of acyclovir alone reduced the % of control by 57.1%, and the plaque count decreased from 109.5 (control) to 47. The results indicate that 1 μg/ml of fusaric acid alone has essentially no effect on HSV-2 infected cells or plaque count. Although the plaque count increased from 94 (control) to 97, the 2% increase in the % of control is within the margin of error and can be attributed to human error.

However, the results indicate that the combination of 6.1 μM of acyclovir and 1 μg/ml fusaric acid reduced the % of control by 70.3%. The plaque count decreased from 109.5 (control) to 32.5. Since 1 μg/ml fusaric acid alone had essentially no effect on HSV-2 infected cells, and 6.1 μM of acyclovir only reduced the % of control by 57.1%, it is surprising that the % of control of the two agents in combination would be reduced by 70.3%. Because 1 μg/ml fusaric acid alone has no effect on HSV-2 infected cells, what would be expected is no improvement over acyclovir by itself or even a counter-additive effect. This 13.2% difference is beyond the error margin and clearly demonstrates synergy in the combination.

With regard to HSV-2, the results indicate that 6.1 μM of acyclovir alone reduced the % of control by 57.1%, and decreased the plaque count from 109.5 (control) to 47. The results indicate that 10 μg/ml of fusaric acid alone has essentially no effect on HSV-2 infected cells or plaque counts. Although the % of control appeared to increased from 94 (control) to 95, the percentage increase is within the margin of error and can be attributed to human error.

However, when combined, the results indicate that the combination of 6.1 μM of acyclovir and 10 μg/ml fusaric acid reduced the % of control by 98.6%, and decreased the plaque count from 109.5 (control) to 1.5. Since 10 μg/ml fusaric acid alone had essentially no effect on HSV-2 infected cells, and 6.1 μM of acyclovir reduced the % of control by only 57.1%, it is surprising that the % of control of the two agents in combination would be reduced by 98.6%. Because 10 μg/ml fusaric acid alone has no effect on HSV-2 infected cells, what would be expected is no improvement over acyclovir by itself, or even a counter-additive effect. This 41.5% difference is well beyond the error margin and clearly demonstrates synergy in the combination.

With regard to HSV-2, the results indicate that at concentrations ranging from 30 μg/ml to 100 μg/ml fusaric acid alone completely eliminated HSV-2 infected cells, and decreased the plaque counts from 94 (control) to 0 over the entire range. Since fusaric acid alone effectively resulted in complete cell death over this range, the combination of fusaric acid in this range and acyclovir cannot show improvement at such high concentrations. The plaque counts cannot be reduced any further.

The data indicates that combinations comprising fusaric acid and acyclovir have a synergistic effect with regard to HSV-1 and HSV-2 infected cells. It is known that at high concentrations, i.e. from 30 μg/ml to 100 μg/ml, fusaric acid alone effectively results in complete cell death for HSV-1 and HSV-2 infected cells. Accordingly, the combination of fusaric acid in this range and acyclovir cannot show improvement at such high concentrations. The plaque counts simply cannot be reduced below zero.

However, the advantage of the claimed combination is that low concentrations of fusaric acid and acyclovir can be combined to effectively treat HSV-1 and HSV-2 infected cells. Accordingly, the claimed combination is more potent, which would benefit patients by making treatment more economical because less drug is required to produce an effective product and administration would be more pleasant since the patient would be required to take less drug.

EXAMPLE 4

Drug Combination of Fusaric Acid and Acyclovir to Treat Dorsal Cutaneous Herpes Simplex Virus I Infection in Guinea Pigs Compounds within the scope of the present invention exhibit marked pharmacological activities according to tests described herein. The results are believed to correlate to pharmacological activity in humans and other animals. The following pharmacological test results are typical characteristics of compounds of the present invention.

Four compounds were prepared for testing in a guinea pig infected with dorsal cutaneous herpes simplex virus I infection: (1) 5% acyclovir (acv) in a liquid vehicle; (2) 5% fusaric acid in a liquid vehicle; (3) 5% acyclovir and 5% fusaric acid in a liquid vehicle; and (4) 20% picolinic acid (pic) having a pH of 3.5 in a liquid vehicle. A control was also prepared that comprised 5% acyclovir in polyethylene glycol, a liquid ointment base. Acyclovir ointment is readily commercially available. The liquid vehicle used was comprised of deionized water (about 47%), petroleum (apx. 22%), mineral oil (apx. 9%), lanolin alcohol (apx. 3%), anhydrous lanolin (apx. 2%) and ceresine wax (140/150) (apx. 7%).

A three-day treatment program was used for all of the compounds tested, including the control. The guinea pigs were prepared in accordance with the protocol described in M. B. McKeough and S. L. Spruance, *Animal Models of Herpes Skin Infection: Guinea-pig*, 209, HANDBOOK OF ANIMAL MODELS OF INFECTION, pages 911–918, herein incorporated by reference in its entirety. HSV-1 virus stock (0.035 ml) was introduced to the guinea pig through its skin at well-spaced sites of equal size on each side of the dorsal midline of a shaved area of the pig by ten activations of a six-pronged spring-loaded vaccination instrument. The day of inoculation was day 0. Approximately 250 mg of each sample compound was applied two times per day for days 1, 2 and 3. In some cases, each sample compound was applied up to four times per day. In the case of the sample that included both acyclovir and fusaric acid, the sample was applied two times per day because of skin irritation. To better see the lesions, a depilatory cream was used to remove regrown hair on the dorsum on day 4. Lesions were then counted and lesions sizes were measured using pictures.

The animals were then sacrificed and the full-thickness skin from different infected treatment areas of the guinea pig were removed. The skin from each of the infected treatment areas was placed into 15 milliliters (mils) of tissue culture medium with 2% Fetal Bovine Serum in an ice bath. The samples were then homogenized in a Stomacher 80 Biomaster lab blender, commercially available from Seward Company, London, United Kingdom. Debris was pelleted by centrifugation and the supernatants collected and frozen at −70° C. until assay for infectivity by plaque formation in VERO cells was performed. The results are summarized in Tables 4a and 4b below.

TABLE 4a

Efficacy Analysis

| | 5% AC V/ Veh | % Diff (p) | Veh | 5% Fusaric Acid | % Diff (p) | Veh | 5% ACV + 5% Fusaric Acid | % Diff (p) | Veh | 20% Pic Acid PH 3.5 | % Diff (p) | Veh |
|---|---|---|---|---|---|---|---|---|---|---|---|---|
| Lesion Number[2] | | | | | | | | | | | | |
| mean | 49 | 6[1] | 52 | 42 | 19 | 52 | 25 | 52 | 52 | 51 | — | 51 |
| sd | 20 | (0.5)[3] | 7 | 12 | (.13) | 7 | 9 | (.02) | 7 | 20 | (.96) | 9 |
| n | 12 | | 12 | 7 | | 12 | 7 | | 12 | 11 | | 12 |
| median | 51.5 | | 53.0 | 41.0 | | 53.0 | 25.0 | | 53.0 | 56.0 | | 52.5 |
| Total Lesion Area mm2 | | | | | | | | | | | | |
| mean | 212 | 20 | 264 | 153 | 41 | 258 | 79 | 71 | 266 | 230 | 18 | 281 |
| sd | 46 | (.005) | 46 | 63 | (.02) | 43 | 31 | (.03) | 47 | 56 | (.02) | 43 |
| n | 12 | | 12 | 7 | | 12 | 6 | | 12 | 11 | | 12 |
| median | 204 | | 273 | 166 | | 270 | 87 | | 279 | 220 | | 277 |
| Titer log (pfu/ml) | | | | | | | | | | | | |
| mean | 4.04 | 46 | 4.31 | 4.03 | 75 | 4.64 | 3.08 | 97 | 4.54 | 4.43 | 41 | 4.66 |
| sd | .41 | (.03) | .43 | .60 | (.02) | .35 | .45 | (.002) | .42 | .39 | (.08) | .40 |
| n | 12 | | 12 | 12 | | 12 | 12 | | 12 | 12 | | 12 |
| median | 4.20 | | 4.36 | 3.98 | | 4.59 | 3.18 | | 4.63 | 4.40 | | 4.64 |

[1]Percent differences between mean lesion seventy at drug-treated sites compared to the vehicle-treated sites are shown A positive value indicates a reduction in lesion severity for the test compound
[2]Day 0 is the day of infection 5% ACV in NVL vehicle, 5% Fusaric Acid, 5% ACV + 5% Fusaric Acid, 50% Picolinic Acid and 5% ACV/PEG were used 2x/day on Days 1, 2 and 3. Efficacy measurements were done on the morning of Day 4.
[3]For statistical analysis, paired data were evaluated by the Wilcoxon signed rank test, utilizing the log means of the drug and vehicle results
[4]nd = not done TABLE 4b

| Efficacy Analysis | | |
|---|---|---|
| 5% ACV/PEG | % Diff (p) | polyethyleneglycol |

| | 5% ACV/PEG | % Diff (p) | polyethyleneglycol |
|---|---|---|---|
| Lesion Number[2] | | | |
| mean | 51 | 4[1] | 53 |
| sd | 9 | (.44)[3] | 7 |
| n | 12 | | 12 |
| median | 55.0 | | 54.5 |
| Total Lesion Area mm2 | | | |
| mean | 183 | 24 | 241 |
| sd | 43 | (.005) | 44 |
| n | 12 | | 12 |
| median | 179 | | 242 |
| Titer log (pfu/ml) | | | |
| mean | 3.98 | 49 | 4.27 |
| sd | .58 | (.01) | .56 |
| n | 12 | | 12 |
| median | 4.08 | | 4.20 |

[1]Percent differences between mean lesion severity at drug-treated sites compared to the vehicle-treated sites are shown. A positive value indicates a reduction in lesion severity for the test compound.
[2]Day 0 is the day of infection. 5% ACV in NVL vehicle, 5% Fusaric Acid, 5% ACV + 5% Fusaric Acid, 50% Picolinic Acid and 5% ACV/PEG were used 2x/day on Days 1, 2 and 3. Efficacy measurements were done on the morning of Day 4.
[3]For statistical analysis, paired data were evaluated by the Wilcoxon signed rank test, utilizing the log means of the drug and vehicle results.

The results indicate that compositions comprising 5% acyclovir as the active agent reduce the number of lesions present by 6%, the total lesion area by 20% and the virus titer by 46%. Compositions comprised of 5% fusaric acid as the active agent significantly reduced the number of lesions present by 19% total lesion area by 41% and virus titer by 75%. Compositions comprised of 5% acyclovir and 5% fusaric acid as the active agents statistically significantly reduced lesion number by 52%, total lesion area by 71% and virus titer by 97%. Compositions that included 20% picolinic acid as the active agent significantly reduced the total lesion area by 18% and the virus titer by 41% and did not show a trend in reducing lesion number.

The Mann-Whitney rank sum test was used to compare the efficacy of the samples. The Mann-Whitney rank sum test is well known to those skilled in the art. The results showed that the compositions that included 5% acyclovir and 5% fusaric acid as the active agents were better than the compositions that comprised 5% acyclovir, 5% fusaric acid and 20% picolinic acid independently as the active agents in all three parameters tested. Further, only the combination of acyclovir and fusaric acid was able to affect all three parameters in a statistically significant manner.

In view of the above, it will be seen that the several objects of the invention are achieved and other advantageous results are obtained. As various changes could be made in the above compounds and methods without departing from the scope of the invention, it is intended that all matters contained in the above description shall be interpreted as illustrative and not in a limiting sense.

We claim:

1. A method of treating a viral disease, disorder, or condition caused by a herpes simplex virus or varicella-zoster virus comprising topically administering to a patient afflicted with said disease, disorder, or condition a therapeutically effective dose of a pharmaceutically acceptable composition comprising (1) about 1.75 $\mu$M acyclovir, a pharmaceutically acceptable salt, solvate or prodrug of acyclovir and (2) about 1 $\mu$g/ml fusaric acid, or a pharmacologically acceptable salt of fusaric acid.

2. A method of treating a viral disease, disorder, or condition caused by a herpes simplex virus or vancella-zoster virus comprising topically administering to a patient afflicted with said disease, disorder, or condition a therapeutically effective dose of a pharmaceutically acceptable composition comprising (1) about 1.75 $\mu$M acyclovir, a pharmaceutically acceptable salt, solvate or prodrug of acyclovir and (2) about 10 $\mu$g/ml fusaric acid, or a pharmacologically acceptable salt of fusaric acid.

3. A method of treating a viral disease, disorder, or condition caused by a herpes simplex virus or varicella-zoster virus comprising topically administering to a patient afflicted with said disease, disorder, or condition a therapeutically effective dose of a pharmaceutically acceptable composition comprising (1) about 6.1 $\mu$M acyclovir, a pharmaceutically acceptable salt, solvate or prodrug of acyclovir and (2) about 1 $\mu$g/ml fusaric acid, or a pharmacologically acceptable salt of fusaric acid.

4. A method of treating a viral disease, disorder, or condition caused by a herpes simplex virus or varicella-zoster virus comprising topically administering to a patient afflicted with said disease, disorder, or condition a therapeutically effective dose of a pharmaceutically acceptable composition comprising (1) about 6.1 $\mu$M acyclovir, a pharmaceutically acceptable salt, solvate or prodrug of acyclovir and (2) about 10 $\mu$g/ml fusaric acid, or a pharmacologically acceptable salt of fusaric acid.

* * * * *